United States Patent
Rosenbauer et al.

(10) Patent No.: US 6,464,798 B1
(45) Date of Patent: Oct. 15, 2002

(54) METHOD AND DEVICE FOR THE TREATMENT OF DISHES IN DISHWASHERS

(75) Inventors: Michael Rosenbauer, Reimlingen; Bruno Reiter, Neresheim-Kösingen; Reinhard Hering, Holzheim; Hans-Georg Bruchmüller, Giengen, all of (DE)

(73) Assignee: BSH Bosch und Siemens Hausgeräte GmbH, Munich (DE)

( * ) Notice: Subject to any disclaimer, the term of this patent is extended or adjusted under 35 U.S.C. 154(b) by 0 days.

(21) Appl. No.: 09/251,824

(22) Filed: Feb. 17, 1999

(30) Foreign Application Priority Data

Feb. 17, 1998 (DE) .......................................... 198 06 559

(51) Int. Cl.[7] .............................. B08B 7/04; B08B 3/00
(52) U.S. Cl. ...................... 134/18; 134/25.1; 134/25.2; 134/56 D; 134/57 D; 134/58 D
(58) Field of Search ...................... 134/18, 25.1, 25.2, 134/56 R, 57 R, 57 D, 58 R, 58 D; 68/12.02; 422/62, 82.09, 73, 74

(56) References Cited

U.S. PATENT DOCUMENTS

| | | | |
|---|---|---|---|
| 5,291,626 A | * 3/1994 | Molnar et al. ................. 8/158 |
| 5,331,177 A | * 7/1994 | Kubisiak et al. ............. 250/574 |
| 5,416,581 A | * 5/1995 | Kanngiesser | |
| 5,477,576 A | * 12/1995 | Berkcan ........................ 8/158 |
| 5,485,013 A | * 1/1996 | Cummins ................... 250/574 |
| 5,506,679 A | 4/1996 | Cooper et al. | |
| 5,586,567 A | * 12/1996 | Smith et al. ............... 134/57 D |
| 5,589,935 A | * 12/1996 | Biard .......................... 356/339 |
| 5,603,233 A | * 2/1997 | Erickson et al. ........... 68/12.02 |
| RE35,566 E | * 7/1997 | Boyer et al. ................... 356/72 |
| 5,731,868 A | * 3/1998 | Okey et al. .................... 356/73 |
| 5,800,628 A | * 9/1998 | Erickson et al. ............. 134/13 |

FOREIGN PATENT DOCUMENTS

| | | |
|---|---|---|
| DE | 37 06 458 C2 | 9/1988 |
| DE | 42 19 276 A1 | 12/1993 |
| DE | 43 42 272 A1 | 6/1995 |
| DE | 195 21 326 A1 | 12/1996 |
| DE | 196 11 402 A1 | 9/1997 |
| DE | 196 45 306 A1 | 11/1997 |
| DE | 196 26 203 A1 | 1/1998 |
| DE | 196 27 594 A1 | 1/1998 |
| DE | 196 29 806 A1 | 1/1998 |
| DE | 197 14 664 A1 | 10/1998 |
| DE | 197 14 695 A1 | 10/1998 |

* cited by examiner

Primary Examiner—Alexander Markoff
(74) Attorney, Agent, or Firm—Laurence A. Greenberg; Werner H. Stemer; Ralph E. Locher

(57) ABSTRACT

A method for treating dishes in a dishwasher comprises the steps of radiating a radiation into a washing liquid in a given direction; detecting a radiation quantity of a radiation emerging from the washing liquid at a given angle with respect to the given direction for at least a given wavelength range; determining data including at least one of a type, a concentration, and a prevailing size of at least one of a dirt component, a cleaning agent component, and suspended particles in the washing liquid on the basis of the detected radiation quantity of the emerging radiation; and optimizing a washing program with the determined data.

25 Claims, 3 Drawing Sheets

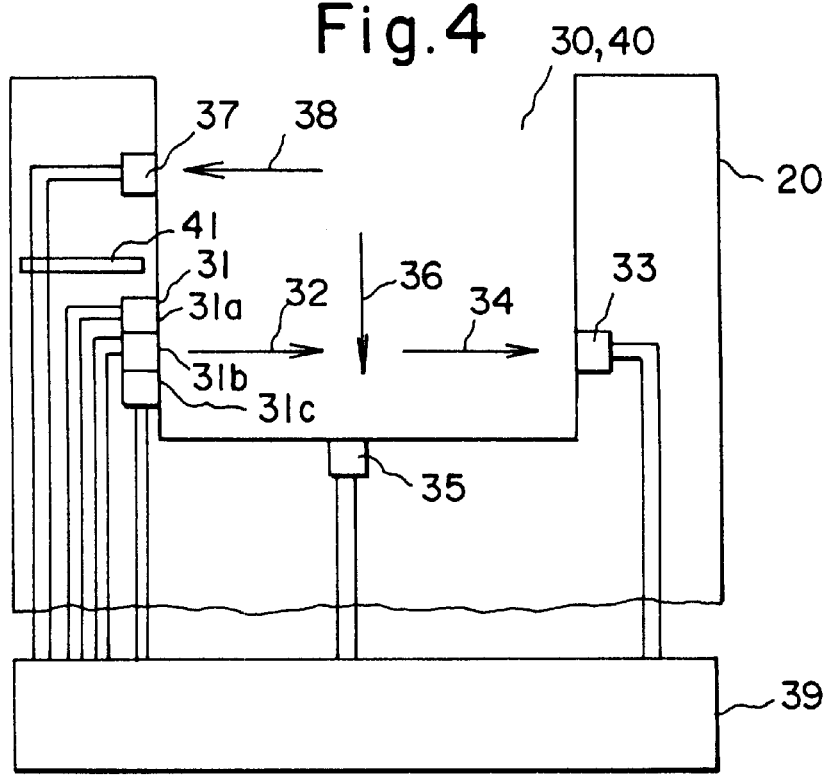
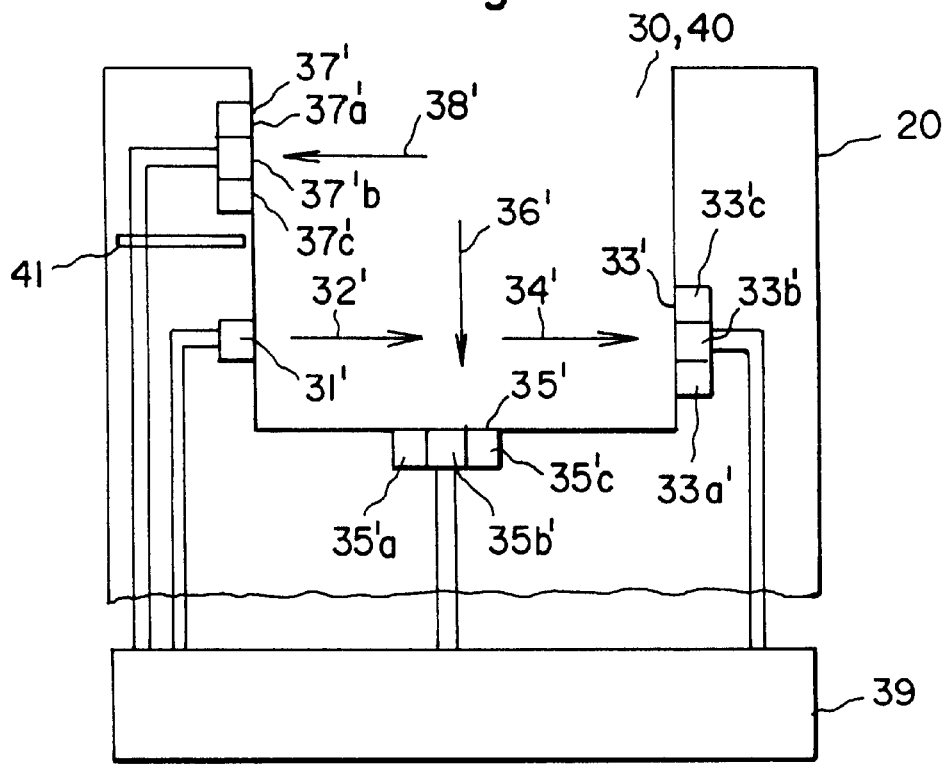

METHOD AND DEVICE FOR THE TREATMENT OF DISHES IN DISHWASHERS

BACKGROUND OF THE INVENTION

FIELD OF THE INVENTION

The invention relates to a method and a device for the treatment of dishes in dishwashers.

The purpose of treating dishes in dishwashers is to remove dirt and crud from the articles to be cleaned. A washing liquid is generally used for this purpose. The washing liquid is mixed with cleaning agents and is preferably sprayed under pressure and at an elevated temperature onto the articles to be cleaned. In the course of a washing program, the washing liquid absorbs the dirt to be removed. Thus the washing liquid becomes thicker and the cleaning-active substances of the cleaning agents are being used up. As a result, the cleaning effect of the washing liquid decreases. Furthermore, where aqueous washing liquids are concerned, the lime content or mineral content of the water also reduces the cleaning effect of the washing liquid due to a partial precipitation of cleaning-active substances.

In order to determine the properties or the state of the washing liquid more accurately, optical turbidity sensors have been proposed for dishwashers. Such sensors are known for instance from the German published patent applications DE 42 43 868 A1, corresponding to U.S. Pat. No. 5,818,063 to Wilhelmstatter et al., and DE 196 11 402 A1. These optical turbidity sensors use light that is sent through the washing liquid. An optical receiver receives the radiation quantity transmitted in a straight line through the washing liquid. These known sensors respond to the turbidity of the washing liquid. With these sensors it is however not possible to determine more precise characteristics of the washing liquid, in particular relating to the type and quantity of its dirt components and/or cleaning agent components, so that this information also cannot be taken into account in controlling the washing program.

A dishwasher having a sensor unit for dirt in a circulated washing liquid is also known from the U.S. Pat. No. 3,888,269. The sensor unit includes an element transmitting optical signals and an element receiving optical signals. The sensor unit is arranged under a transparent portion of a horizontal shoulder of a treatment vessel, the transparent portion being surrounded by an upstanding rim.

Despite the movement of the circulated washing liquid, deposits of dirt particles may accumulate on the horizontal shoulder of the treatment vessel. Particularly the upstanding rim of the transparent portion causes dirt particles to accumulate precisely in the region in which the sensor unit is measuring. The washing liquid remaining on the horizontal shoulder evaporates. Due to the high temperatures in the dishwasher during the washing program cycle, the evaporation is even advanced. Depending on the degree of hardness of the washing liquid used, a lime deposit occurs when the remaining washing liquid evaporates. Particularly the upstanding rim of the transparent portion described above leads, in the region in which the sensor unit is measuring, to accumulations of the washing liquid which leaves behind lime deposits in the measuring region of the sensor unit during evaporation. Deposits of lime and accumulations of dirt particles on the transparent portion lead to false measurement result of the sensor unit. On the horizontal shoulder of the treatment vessel described above, a proper exchange or circulating of the washing liquid does not take place, so that the degree of dirt actually present in the washing liquid is not detected. As a result, the sensor unit generates false measurements. Particularly the upstanding rim of the transparent portion described above leads, precisely in the region in which the sensor unit is measuring, to accumulations of washing liquid which, if they remain for a relatively long time, do not have the degree of dirt actually present in the washing liquid, thus leading to false measurement results of the sensor unit.

SUMMARY OF THE INVENTION

It is accordingly an object of the invention to provide a method and a device for the treatment of dishes in dishwashers which overcomes the above-mentioned disadvantages of the heretofore-known methods and devices of this general type and, in which, by means of an optical method, more accurate data on the dirt components and/or cleaning agent components of the washing liquid can be determined and taken into account in the optimization or control of the washing program. With the foregoing and other objects in view there is provided, in accordance with the invention, a method for treating dishes in a dishwasher, which comprises: radiating a radiation into a washing liquid in a given direction; detecting a radiation quantity of a radiation emerging from the washing liquid at a given angle with respect to the given direction for at least a given wavelength range; determining data including at least one of a type, a concentration, and a prevailing size of at least one of a dirt component, a cleaning agent component, and suspended particles in the washing liquid on the basis of the detected radiation quantity of the emerging radiation; and optimizing a washing program with the determined data.

In accordance with a further feature of the invention, the given wavelength range is substantially a wavelength range of a single wavelength.

In accordance with a further feature of the invention, the step of detecting includes detecting the radiation quantity of the radiation emerging from the washing liquid substantially in the given direction, and the step of determining data is further based on a radiation quantity of the radiation radiated into the washing liquid.

In accordance with a further feature of the invention, the step of detecting includes detecting the radiation quantity of the radiation emerging as a scattered radiation from the washing liquid substantially perpendicular to the given direction, and the step of determining data is further based on a radiation quantity of the radiation radiated into the washing liquid.

In accordance with a further feature of the invention, the step of detecting includes detecting the radiation quantity of the radiation emerging as a backscattered radiation from the washing liquid substantially opposite to the given direction, and wherein the step of determining data is further based on a radiation quantity of the radiation radiated into the washing liquid.

In accordance with a further feature of the invention, the radiation radiated into the washing liquid includes at least the given wavelength range, and the radiation quantity of the radiation emerging from the washing liquid is determined by at least one broadband radiation receiver sensitive to a wide wavelength range including the given wavelength range.

In accordance with a further feature of the invention, the radiation radiated into the washing liquid is generated by a plurality of radiation sources, the given wavelength range including a plurality of partial wavelength ranges, and the given partial wavelength ranges is generated by a respective one radiation source of the plurality of radiation sources.

In accordance with a further feature of the invention, the radiation radiated into the washing liquid includes at least the given wavelength range, and the radiation quantity of the radiation emerging from the washing liquid is determined by at least one radiation receiver sensitive to the given wavelength range.

In accordance with a further feature of the invention, the radiation radiated into the washing liquid is generated by a broadband radiation source generating all wavelength ranges to be emitted.

In accordance with a further feature of the invention, the radiation radiated into the washing liquid is emitted in at least one wavelength range, in which the at least one of a dirt component, a cleaning agent component, and suspended particles in the washing liquid causes at least one of a pronounced attenuation and scattering of the radiation radiated into the washing liquid.

In accordance with a further feature of the invention, the step of radiating the radiation into the washing liquid includes sequentially emitting a first wavelength range and a second wavelength range.

In accordance with a further feature of the invention, the step of detecting includes sequentially detecting the radiation quantity of a radiation having a first wavelength range and detecting the radiation quantity of a radiation having a second wavelength range.

In accordance with a further feature of the invention, the radiation radiated into the washing liquid is emitted in a pulsed manner.

In accordance with a further feature of the invention, the radiation radiated into the washing liquid is emitted with a wavelength range of substantially a single wavelength.

In accordance with a further feature of the invention, the radiation radiated into the washing liquid is guided to the washing liquid by a radiation guide.

In accordance with a further feature of the invention, the radiation emerging from the washing liquid is guided to at least one radiation receiver via a radiation guide.

The object of the invention is achieved, according to the invention, in that radiation is radiated into a washing liquid, in that the radiation quantity of the radiation reemerging in each case at a respective predetermined angle is determined or recorded for at least one wavelength range and preferably for one wavelength, in that, based on the reemerging radiation, the type and concentration of dirt components and/or cleaning agent components of the washing liquid are determined, and in that the washing program is optimized by these determined data.

The radiation quantity or radiation intensity, the color or wavelength, the polarization or the spectrum may for example be determined as characteristics of the reemerging radiation. In this case, the reemerging radiation quantity or radiation intensity can be determined as a function of the irradiated radiation quantity and can be standardized so as, in particular, to have a magnitude which can be handled in a simple way for further evaluation.

The analysis of the reemerging radiation is carried out for at least one specific wavelength, so that, depending on the wavelength used or on the wavelengths used, the type and concentration of highly specific dirt components and/or cleaning agent components of the washing liquid can be detected. Irrespective of this, the characteristics of the reemerging radiation can be determined for at least one specific angle of emergence, so that the number of measured parameters and, consequently, of determinable items of information on the dirt components and/or cleaning agent components can be increased. Finally, the state or condition of the washing liquid is gathered from the type, magnitude and concentration of dirt components and/or cleaning agent components.

The state of the washing liquid and, in particular, the content of cleaning agents and of already absorbed dirt, crud and impurities, together with other parameters, such as, for example, temperature, the duration of the washing program or the duration of the circulation of the washing liquid, are critical for the cleaning power and the course of the washing program. Information on the state of the washing liquid is therefore particularly useful for optimizing the washing program. Thus, if the cleaning agent concentration is known as a function of various factors, such as, for example, the water hardness, degree of dirt or type of dirt of the articles to be cleaned, the cleaning agent can be metered as required, and, if the cleaning agent concentration is monitored continuously, can even, where appropriate, be additionally metered in subsequent steps. From the time profile of the cleaning agent concentration, for example from the rate of decrease in the concentration, conclusions can be drawn as to the quantity or type of dirt contained in the washing liquid or else as to the instantaneous dirt level or impurity level of the articles to be cleaned. If, for example, the cleaning agent content no longer decreases or the impurities in the washing liquid no longer increase, it may be concluded from this that impurities can no longer be removed from the articles to be cleaned and the washing program or the corresponding subprogram step of the washing program can be terminated at this point.

The same also applies accordingly if the properties of the various impurities in the washing liquid are known. If there are different cleaning agents available, these cleaning agents likewise have to be added only as required, due to the possible determination not only of the quantity, but also of the type of impurities contained in the washing liquid.

Furthermore, it is also possible to renew the washing liquid when a specific degree of dirt is reached.

The optimization of the washing program on the basis of different information on the state of the washing liquid may also include other parameters, such as, for example, the temperature of the washing liquid, the type or duration of the washing program, the change of the washing liquid, the addition of water, etc.

An additional advantage afforded in the case of an optical method is that direct contact between the structural parts and the washing liquid can be avoided by simple means. Thus, for this purpose, the washing liquid needs to flow only through a region, around which, at different locations, the structural parts for emitting the radiation or for determining the characteristics of the radiation reemerging at a specific angle are arranged. Corrosion or soiling of the structural elements due to contact with washing liquid can be avoided in this way.

In one embodiment, the radiation quantity transmitted in an essentially straight direction through the washing liquid is determined, and the concentration of at least one dirt component and/or cleaning agent component and/or the prevailing magnitude of the suspended particles in the washing liquid is determined as a function of the radiation quantity emitted.

In this case of a simple measurement of the radiation quantity transmitted in an essentially straight direction, the transmission value of the washing liquid is determined for at least one specific wavelength, and this can be carried out by very simple means. Nevertheless, the concentration of dirt components and/or cleaning agent components and/or the prevailing magnitude of the suspended particles in the washing liquid can be determined reliably from the transmission value measured for a specific wavelength or for a plurality of specific wavelengths.

In another embodiment, the radiation quantity, which is scattered laterally essentially perpendicularly to the direction in which the radiation is radiated into the washing liquid, is determined, and the concentration of at least one dirt component and/or cleaning agent component and/or the prevailing magnitude of the suspended particles in the washing liquid is determined as a function of the radiation quantity emitted.

The lateral scattering due to the dirt components and/or cleaning agent components depends on various factors, such as, for example, the wavelength, the particle magnitude, the concentration or type of dirt components and/or cleaning agent components. In order to determine the various characteristics of the dirt components and/or cleaning agent components, the dependencies of the lateral scatter on the various factors may be utilized. Thus, the intensity of the lateral scatter is, in particular, proportional to the concentration of the dirt components and/or cleaning agent components, so that the concentration of specific dirt components and/or cleaning agent components can also be determined from the laterally scattered radiation quantity in the case of at least one specific wavelength. Since the lateral scattering greatly depends on the magnitude of the suspended particles or on the wavelength of the radiation used, conclusions as to the type and magnitude of the suspended particles may be drawn, in particular, by using radiation of widely differing wavelengths.

For suspended particles, therefore, there is a relation between the scatter value and the wavelength; in particular, the scatter decreases when the wavelength increases in comparison with the particle magnitude. In this way, the prevailing magnitude of the suspended particles can be determined by measuring the lateral scatter for a plurality of different wavelengths. An especially striking increase in the lateral scatter occurs, in particular, when the condition: "particle magnitude less than wavelength" is satisfied.

Furthermore, the radiation quantity, which is backscattered essentially opposite to the direction in which the radiation is radiated into the washing liquid, is also determined, and the concentration of at least one dirt component and/or cleaning agent component and/or the prevailing magnitude of the suspended particles in the washing liquid is determined as a function of the radiation quantity emitted.

For this case of backscattering or reflection, in principle the same applies as to lateral scattering. In this case, by measuring the backscatter, additional parameters can be obtained, which can be used to determine the dirt components and/or cleaning agent components of the washing liquid.

In general, the radiation quantities reemerging in various directions are determined, on the basis of transmission or scatter, for at least one wavelength range, so that, overall, a set of values, which is evaluated by means of rules, is obtained as a function of the number of wavelengths used and of the evaluated angles of emergence. As a result, the characteristics of the dirt components and/or cleaning agent components can be determined from this. The rules for evaluation may be, in particular, empirical values which are arrived at in practice and are determined once for various known washing liquid compositions for the wavelengths and angles of emergence used in the method and with which the measurement results from unknown washing liquid compositions are then compared.

According to a preferred embodiment of the invention, the radiation emitted in each case contains only the at least one wavelength range of preferably one wavelength, and the transmitted and/or laterally scattered and/or backscattered radiation quantity is determined in each case by at least one broadband radiation receiver sensitive to all the wavelength ranges emitted, expediently the radiation with at least one wavelength range of preferably one wavelength being generated by at least one radiation source, each wavelength range being generated in each case by at least one radiation source which transmits in this wavelength range.

As an alternative to this, according to a further advantageous embodiment of the invention, the emitted radiation contains the at least one wavelength range, in each case of preferably one wavelength, and the transmitted and/or laterally scattered and/or backscattered radiation quantity is determined in each case by at least one radiation receiver sensitive to the wavelength range emitted, expediently the radiation with at least one wavelength range of preferably one wavelength being generated by a broadband radiation source generating all the wavelength ranges to be emitted.

Preferably, radiation is emitted in the wavelength range or in the wavelength ranges, in which the at least one dirt component and/or cleaning agent component of the washing liquid, the type and concentration of which component are to be determined, leads to a pronounced attenuation and/or scattering of the irradiated radiation. In such an instance, an observed attenuation and/or scattering of the radiation can be associated to a great extent with a specific dirt component and/or cleaning agent component, the characteristics of which can then be determined with a reduced influence of disturbance variables, such as, for example, even other dirt components and/or cleaning agent components.

Advantageously, the respective radiation in at least one emitted wavelength range is emitted and/or determined after the respective radiation in another emitted wavelength range. By virtue of this measure of a successive emission of the radiation or a successive determination of the incoming radiation quantity, an intermixing of the wavelengths is avoided and unequivocal measurement results are achieved.

It is also particularly advantageous to emit the radiation in a pulsed manner. In this way, in the case of a usually low continuous capacity of the radiation sources, a considerably higher radiation pulse capacity can be achieved, which leads to higher signal intensities and improved signal-to-noise ratios. Particularly when the transmitted or scattered radiation quantity is small, for example on account of high turbidity or a low scatter coefficient, low signal levels can be raised in this way, thus simplifying the processing of the signals and increasing the degree of accuracy.

It has proved particularly expedient, in practice, to emit the radiation in a wavelength range of essentially one wavelength. Thus, at least the one wavelength with which the washing liquid is investigated can then be fixed or appointed by selecting at least the one narrowband radiation source. In the case of a plurality of radiation sources, as described above, these are advantageously activated in succession or in changing combinations, so that the recorded radiation quantities can be assigned to the individual radiation sources and, consequently, to wavelength ranges.

In a further embodiment, it may be envisaged that the emitted radiation is guided to the washing liquid and/or the radiation transmitted and/or scattered by the washing liquid is guided to the at least one radiation receiver via radiation guides. In this way, at least one of the radiation sources and at least one of the radiation receivers can be arranged spatially independently or separated from the washing liquid which is to be investigated. In particular, it is thereby possible to integrate at least one of the radiation sources and at least one of the radiation receivers in a central electronic unit. Consequently, higher operating reliability and a reduction in electric lines laid in the dishwasher can be achieved.

Moreover, the invention relates to a device for carrying out the method according to the invention and to a dishwasher which is equipped with such a device.

A further objective of the invention is therefore providing, in a simple manner, a device for carrying out the above-described method for the treatment of dishes in dishwashers, in which, furthermore, faulty measurements of a sensor for dirt in a circulated washing liquid are avoided.

In accordance with the invention there is provided a device operating in accordance with the method of the invention for determining at least one of a type, a concentration, and a prevailing size of at least one of a dirt component, a cleaning agent component, and suspended particles in a washing liquid of a dishwashers, the device comprises at least one radiation source emitting radiation in at least one wavelength range into a washing liquid; at least one radiation receiver for determining a radiation quantity of a radiation emerging from the washing liquid and generating a signal corresponding to the radiation quantity; and at least one control and evaluation unit connected to the at least one radiation source and connected to the at least one radiation receiver for controlling the at least one radiation source and for evaluating the signal from the at least one radiation receiver.

In accordance with a further feature of the invention, the at least one wavelength range is a wavelength range of a single wavelength.

In accordance with a further feature of the invention, the at least one radiation receiver determines the radiation quantity of at least one of a radiation transmitted through the washing liquid, a radiation laterally scattered in the washing liquid, and a radiation backscattered in the washing liquid.

In accordance with a further feature of the invention, the at least one radiation source emits the radiation in a given direction, the at least one radiation receiver including a first radiation receiver for determining the radiation quantity of the transmitted radiation at an angle of substantially 180° with respect to the given direction, a second radiation receiver determining the radiation quantity of the laterally scattered radiation at an angle of substantially 90° with respect to the given direction, and a third radiation receiver determining the radiation quantity of the backscattered radiation at an angle of substantially 0° with respect to the given direction.

In accordance with a further feature of the invention, there is provided a flow heater, the at least one radiation source and the at least one radiation receiver forming a sensor unit, the sensor unit disposed in the flow heater.

In accordance with a further feature of the invention, there is provided a receptacle, the sensor unit placed in the receptacle.

In accordance with a further feature of the invention, the flow heater has a separate receiving connection piece for receiving the sensor unit placed in the receptacle, the receptacle being formed from at least a milky-transparent material, being completely closed at an end thereof projecting into the flow heater, and having a substantially round cross section.

In accordance with a further feature of the invention, there is provided a printed circuit board having two side legs and one connecting leg and having a U-shaped recess formed therein, the sensor unit being fastened on the printed circuit board, wherein the at least one radiation receiver is a plurality of radiation receivers, each respective one of the radiation receivers disposed on a respective one of the side legs and the connecting leg and directed toward the U-shaped recess, the at least one radiation source disposed on one of the side legs.

In accordance with a further feature of the invention, the receptacle has two legs disposed at a given distance from one another, the side legs of the printed circuit board disposed in the legs of the receptacle, the legs of the receptacle having a cross-sectional shape of two circle segments resting with chords thereof against one another, the receptacle having wall portions, behind which the radiation receivers and the at least one radiation source are disposed, the wall portions having a wall thickness less than a wall thickness of a remaining part of the receptacle.

In accordance with a further feature of the invention, the receptacle has at least one guide, into which the printed circuit board can be inserted, the guide including holding ribs disposed in pairs at a distance from one another corresponding to a thickness of the printed circuit board.

In accordance with a further feature of the invention, there is provided a radiation guide for guiding the radiation radiated into the washing liquid from the at least one radiation source to the receptacle.

In accordance with a further feature of the invention, there is provided a radiation guide for guiding the radiation emerging from the washing liquid from the receptacle to the at least one radiation receiver.

A device according to the invention for carrying out the method of the invention has at least one radiation source which emits radiation in at least one wavelength range of preferably one wavelength, at least one radiation receiver for determining the radiation quantity transmitted and/or laterally scattered and/or backscattered by the washing liquid, and at least one unit for activating the at least one radiation source and for evaluating the signal from the at least one radiation receiver. Since present-day dishwashers, as a rule, in any case have a central electronic control unit, the unit for activating at least one of the radiation sources and for evaluating the signal from at least one of the radiation receivers is advantageously integrated into this central unit or the activation of at least one of the radiation sources and the evaluation of the signal from at least one of the radiation receivers are performed by the central unit.

Advantageously, as seen from the radiation emitted by the radiation source, the angle in each case between the at least one radiation source and the at least one radiation receiver for determining the transmitted radiation quantity is essentially 180°, the angle in each case between the at least one radiation source and the at least one radiation receiver for determining the laterally scattered radiation quantity is essentially 90°, and the angle in each case between the at least one radiation source and the at least one radiation receiver for determining the backscattered radiation quantity is essentially 0°. It is necessary, at the same time, to ensure that, in order to determine the backscattered radiation quantity, the radiation receiver should be arranged as near as possible to the one associated radiation source, but must be sufficiently shielded from this, in order to avoid direct irradiation.

According to a further preferred embodiment of the invention, the sensor unit consisting in each case of the at least one radiation source and the at least one radiation receiver is arranged in a flow heater.

A flow heater is a means for heating the circulated washing liquid of a dishwasher, the means being arranged in the flow path of the circulated washing liquid. Consequently, during sub-program steps with circulation and heating of the washing liquid, the flow heater has flowing through it constantly washing liquid which has the degree of dirt which is actually present in the washing liquid and which can be detected by the sensor unit. An accumulation of dirt is ruled out completely on account of the constant throughflow. Normally, the flow heater remains completely full of washing liquid even during circulation intermissions and even when the dishwasher is at a standstill, so that evaporation of a residual quantity of a washing liquid and, consequently, a deposit of lime precipitated during evaporation do not take place. According to the invention, the sensor unit for dirt in a circulated washing liquid is arranged at a point where there is a defined exchange of washing liquid and where there is no risk that dirt or lime will be deposited. The arrangement according to the invention of the sensor unit in a flow heater provides in a simple way a dishwasher with a device for carrying out the method according to the invention, in which faulty measurements of a sensor for dirt in a circulated washing liquid are avoided effectively.

It is particularly advantageous if the sensor unit is arranged in a receptacle. This measure achieves additional protection of the sensor unit and simplification of the mounting of the sensor unit in the flow heater, since premounting and even simple insertion of the sensor unit become possible.

Expediently, the flow heater has a separate receiving connection piece for the sensor unit which is introduced into the receptacle, the receptacle having essentially a round cross section and being produced from at least milky-transparent material, and the receptacle being completely closed at its end projecting into the flow heater. Arranging a separate receiving connection piece on the flow heater achieves a further simplification in the design of the flow heater and also in the mounting of the latter, since premounting and even simple insertion of the sensor unit become possible. The round cross section of the receptacle further simplifies the design of the receiving connection piece and, consequently, the manufacture of the flow heater and also of the receptacle. By virtue of the at least milky-transparent material used for the receptacle, a further possible fault source, specifically the influence of the material to be penetrated by the optical signals, is ruled out as far as possible. By means of the completely closed end, direct contact of the sensor unit by the washing liquid is avoided and, consequently, additional reliability in the functioning of the sensor is ensured.

According to a further embodiment of the invention, the sensor unit is fastened on a printed circuit board having a U-shaped recess consisting of two side legs and of one connecting leg, in each case at least one of the radiation receivers being arranged on each leg of the U-shaped recess and being directed toward the U-shaped recess, and the at least one radiation source being arranged on one side leg of the U-shaped recess. Simplified production and mounting of the sensor are achieved by means of this embodiment.

In a particularly advantageous way, the receptacle has two legs which are arranged at a distance from one another and in which a side leg of the printed circuit board is arranged in each case, the legs having essentially a cross-sectional shape of circle segments resting with their chords one against the other, and in each case a wall portion, behind which a radiation receiver or a radiation source is arranged, having a smaller wall thickness than the wall thickness of the remaining parts of the receptacle. The legs arranged at a distance from one another define a better measuring section than the prior art described above, since the optical signals from the radiation source to the radiation receiver penetrate essentially only the washing liquid to be assessed which flows through between the two legs. Since the legs of the receptacle have essentially a cross-sectional shape of circle segments resting with their chords one against the other, a sharp outer edge is formed and all the outer faces of the legs are rounded, and the settling of deposits is largely ruled out. In order, as far as possible, to rule out a further possible fault source, specifically the influence or action of the material to be penetrated by the optical signals, in each case one wall portion of the leg walls forming the boundary of the interspace has a smaller wall thickness than the wall thickness of the remaining parts of the receptacle.

Expediently, the receptacle has at least one guide, into which the printed circuit board can be pushed, the guide consisting of holding ribs arranged in pairs at a distance from one another corresponding to the thickness of the printed circuit board, thus making it possible for the sensor unit to be mounted even more easily and allowing the receptacle to be produced in a simple way.

In a further embodiment of the invention, the radiation from the at least one radiation source to the receptacle and/or from the receptacle to at least one radiation receiver is guided via radiation guides. In this way, at least one of the radiation sources and at least one of the radiation receivers can be arranged spatially independently of the washing liquid which is to be investigated.

Other features which are considered as characteristic for the invention are set forth in the appended claims.

Although the invention is illustrated and described herein as embodied in a method and device for the treatment of dishes in dishwashers, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 4 is a schematic view of a design of a device according to the invention with a broadband radiation source and three radiation receivers for measuring the transmitted and the laterally scattered or backscattered radiation quantity; and FIG. 5 is a schematic view of a further design of a device according to the invention with a radiation source and three radiation receivers for measuring the transmitted and the laterally scattered or backscattered radiation quantity.

DESCRIPTION OF THE PREFERRED EMBODIMENTS

Figure 1:
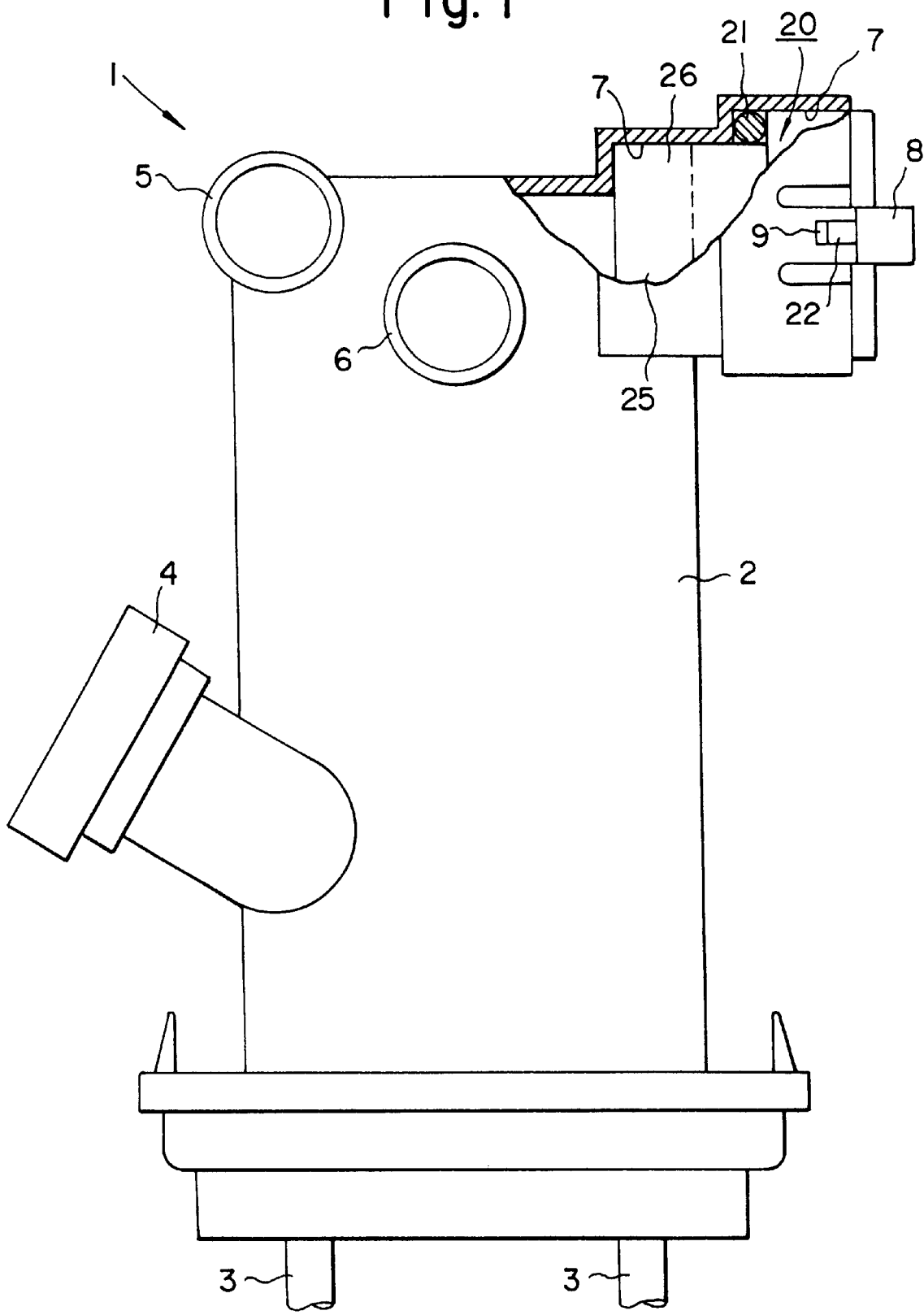
FIG. 1 is a schematic illustration of a flow heater of a water-carrying domestic appliance according to the invention.

Referring now to the figures of the drawings in detail and first, particularly, to FIG. 1, there is seen a flow heater 1 of a dishwasher, that is not described in detail, for heating a circulated washing liquid 40, the flow heater having heating elements 3 arranged in a closed housing 2, an inlet connection piece 4 and at least one outlet connection piece. In the exemplary embodiment there are two outlet connection pieces 5, 6 shown.

According to the two exemplary embodiments, a sensor unit 10 for dirt in the circulated washing liquid 40 is arranged in the flow heater 1. The sensor includes a radiation source 31, 31' and three radiation receivers 33, 33', 35, 35', 37, 37'. For this purpose, the flow heater 1 has a separate receiving connection piece 7 for the sensor unit 10, in which the sensor unit 10, which is inserted into a milky-transparent receptacle 20 having an essentially round cross section, is introduced and is sealed off by means of an O-ring 21. The receptacle 20 is fastened to the flow heater 1 by means of a snap connection which consists of two spring tabs 8 projecting from the receiving connection piece 7 and each having an orifice 9, into which a catch boss 22 of the receptacle 20 drops in each case.

Figure 2:
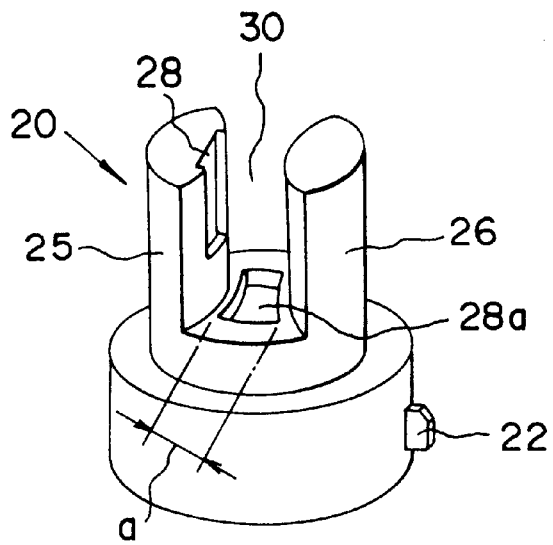
FIG. 2 is an exploded view of an arrangement of a sensor in a receptacle.

As can be seen in FIG. 2, the sensor unit 10 is fastened on a printed circuit board 11, the elements 31, 31', 33, 33', 35, 35', 37, 37' of the sensor unit 10 being arranged in clamping receptacles 12, 13, 14, 15, the feed lines of which are in each case fastened by means of holding devices and guides, which are not described in any more detail, at that end of the printed circuit board 11 which is located opposite the clamping receptacles 12, 13, 14, 15, in each case by means of two-part connecting terminals 16, 17, 18, 19.

The printed circuit board 11 has a U-shaped recess consisting of two side legs and of one connecting leg. In the exemplary embodiments shown, in each case one of the radiation receivers 33, 33', 35, 35', 37, 37' is arranged on each leg of the U-shaped recess and is directed toward the U-shaped recess and the radiation source 31, 31' is arranged on one side leg of the U-shaped recess.

Figure 3:
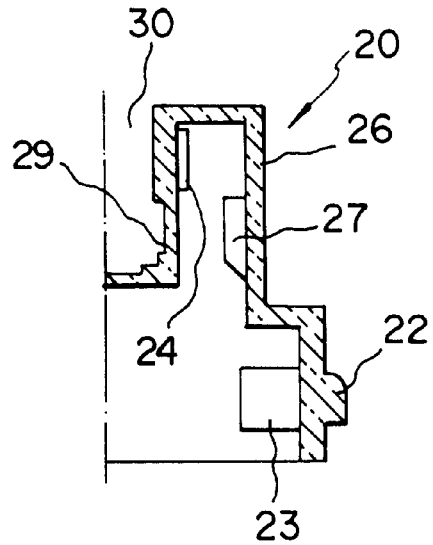
FIG. 3 is a half-sectional view of a receptacle.
Figure 3:
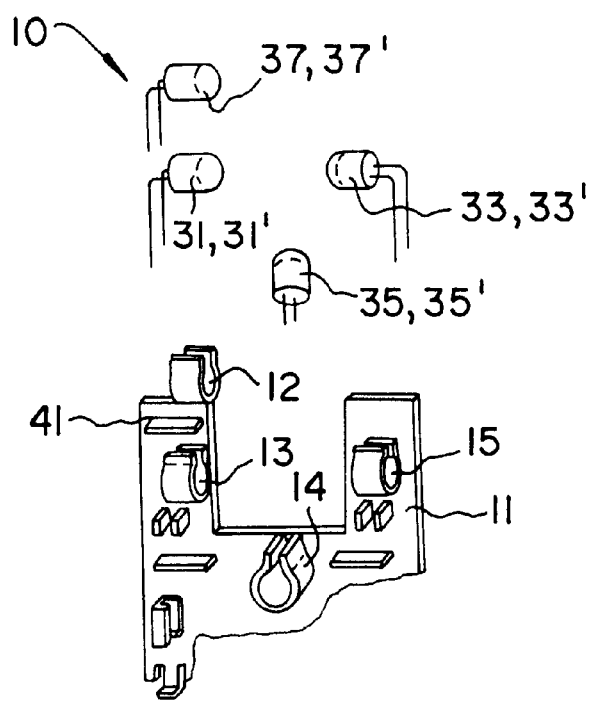
Figure 3:
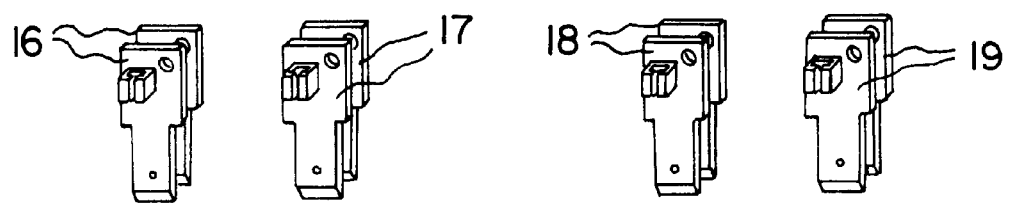

As can be seen in FIG. 3, the receptacle 20 has guides, into which the printed circuit board 11 can be pushed. The guides include holding ribs 23, 24 arranged in pairs at a distance from one another corresponding to the thickness of the printed circuit board 11.

The receptacle 20 has two legs 25, 26 arranged at a distance from one another, with the result that an interspace 30, which constitutes the measuring section of the sensor unit 10, is formed. The elements 31, 31', 33, 33', 35, 35', 37, 37' of the sensor unit 10 are therefore arranged in the legs 25, 26, as can be seen most clearly in FIG. 2. In the exemplary embodiments shown, the legs 25, 26 have, in cross section, essentially a shape of circle segments resting with their chords one on the other. Arranged in each leg 25, 26 are fixing ribs 27 (FIG. 3) which press the corresponding element 31, 31', 33, 33', 35, 35' of the sensor unit 10 into bearing contacts on the opposite inner wall of the corresponding leg 25, 26. In each case one wall portion 28, 28a, 29 of the walls of the receptacle 20 which form the boundary of the interspace 30, on which wall portion the corresponding element 31, 31', 33, 33', 35, 35', 37, 37' of the sensor unit 10 bears, has a smaller wall thickness than the wall thickness of the remaining parts of the receptacle 20 as can be seen most clearly in FIG. 3.

A shield 41 is arranged between the clamping receptacles 12, 13 located on one side leg of the U-shaped recess.

The flow heater 1 is arranged in the flow path of the circulated washing liquid 40 of the dishwasher for the purpose of heating the circulated washing liquid 40. Consequently, during sub-program steps with circulation and heating of the washing liquid, the flow heater 1 has the washing liquid 40 flowing through it constantly. This washing liquid 40 flowing through the flow heater 1 has the degree of dirt which is actually present in the washing liquid 40, so that the sensor unit 10 can detect this. An accumulation of dirt is ruled out completely on account of the constant throughflow. Normally, the flow heater 1 remains completely full of washing liquid 40 during circulation intermissions and even when the dishwasher is at a standstill, so that evaporation of a residual quantity of a washing liquid 40 and, consequently, a deposit of lime precipitated during evaporation do not take place. The sensor unit 10 for dirt in the circulated washing liquid 40 is arranged at a point where there is a defined exchange of washing liquid and where there is no risk that dirt or lime will be deposited. The arrangement of the sensor unit 10 in the flow heater 1 provides in a simple way a dishwasher for carrying out the method according to the invention, in which faulty measurements of the sensor unit 10 are avoided effectively.

FIG. 4 illustrates schematically a preferred embodiment of the sensor unit 10 according to the invention, the elements 31, 33, 35, 37 of which are arranged, in the way described with reference to FIG. 3, around the U-shaped cutout of the printed circuit board 11 pushed into the receptacle 20. Radiation 32 with three wavelength ranges in the exemplary embodiment, namely green visible light radiation, infrared radiation and ultraviolet radiation, is generated, in this preferred embodiment, by a broadband radiation source 31 having three radiation sources 31a, 31b, 31c and generating all the wavelength ranges to be emitted. In the exemplary embodiment, the radiation 32 is transmitted into the interspace 30 of the receptacle 20, through which interspace the washing liquid 40 flows, that is to say, is transmitted into the washing liquid 40. The three radiation sources 31a, 31b, 31c of the radiation source 31 and the radiation receivers 33, 35 and 37 are connected to a control and evaluation unit 39. The latter activates the three radiation sources 31a, 31b, 31c of the radiation source 31 in succession, so that the radiation 32 is generated in succession by the three radiation sources 31a, 31b, 31c. As a result, the radiation quantities measured in each case by means of the radiation receivers 33, 35 and 37, which are broadband in the exemplary embodiment and which are sensitive to all the wavelength ranges emitted, can be assigned unequivocally to the wavelength just emitted. The radiation 32 radiated into the washing liquid 40 either is transmitted there and arrives as transmitted radiation 34 at the radiation receiver 33, or is scattered laterally and arrives as laterally scattered radiation 36 at the radiation receiver 35, or is reflected and arrives as backscattered radiation 38 at the radiation receiver 37. According to the spatial arrangement, already described above, of the individual elements of the sensor unit 10 according to this exemplary embodiment, as seen from the radiation 32 emitted by the radiation source 31, the angle between the radiation source 31 and the radiation receiver 33 for determining the transmitted radiation quantity 34 is essentially 180°, the angle between the radiation source 31 and the radiation receiver 35 for determining the laterally scattered radiation quantity 36 is essentially 90°, and the angle between the radiation source 31 and the radiation receiver 37 for determining the backscattered radiation quantity 38 is essentially 0°. In order to avoid direct irradiation by the radiation source 31 of the radiation receiver 37 for determining the backscattered radiation quantity 38, which radiation receiver should be arranged as close as possible to the radiation source 31, a shield 41 is provided between the radiation source 31 and the radiation receiver 37. The radiation quantity of the radiation measured in each case by the radiation receivers 33, 35, 37 corresponds to the respective spatial arrangement of the radiation source 31 and the radiation receivers 33, 35, 37 and corresponds to the transmitted radiation 34 transmitted through the washing liquid 40 and the receptacle 20, the laterally scattered radiation 36, or the backscattered radiation 38. The receptacle 20 is formed, as already described above, from a material transparent to the emitted wavelength, so that its absorption can be ignored. The current generated in the radiation receivers 33, 35, 37 by the radiation 32 is proportional to the incident radiation quantity and is measured by the control and evaluation unit 39. In the case of the three radiation receivers 33, 35, 37 used in the exemplary embodiment shown, nine values are therefore determined with the three different wavelengths in the exemplary embodiment. The control and evaluation unit 39 then calculates in each case the ratio of the respectively measured radiation quantity to the respectively emitted radiation quantity and, on the basis of these ratio values, determines the characteristics of the dirt components and/or cleaning agent components of the washing liquid 40. With reference to the determined characteristics of the dirt components and/or cleaning agent components, the washing program is optimized, for example by controlling the addition of cleaning agents, the washing liquid quantity, the change of washing liquid and the temperature of the washing program of the dishwasher.

FIG. 5 schematically illustrates a further embodiment of a sensor unit 10 according to the invention, the elements 31', 33', 35', 37' of the sensor unit are arranged, in the way described with reference to FIG. 3, around the U-shaped cutout of the printed circuit board 11 pushed into the receptacle 20. Radiation 32' with three wavelength ranges in the exemplary embodiment, namely green visible light radiation, infrared radiation and ultraviolet radiation, is generated, in this embodiment according to FIG. 5, by a single broadband radiation source 31' generating all the wavelength ranges to be emitted. As in the exemplary embodiment shown in FIG. 4, in this exemplary embodiment too, the radiation 32' is transmitted into the interspace 30 of the receptacle 20, through which interspace the washing liquid 40 flows. In other words, the radiation 32' is transmitted into the washing liquid 40. The radiation source 31' and the radiation receivers 33', 35' and 37' are connected to a control and evaluation unit 39. The latter activates the radiation source 31'. The radiation source 31', then, radiates the radiation 32' with all the wavelength ranges into the interspace 30 of the receptacle 20 and consequently into the washing liquid 40. As described in respect of the exemplary embodiment according to FIG. 4, the radiation 32' radiated into the washing liquid 40 either is transmitted there and arrives as transmitted radiation 34' at the radiation receiver 33', or is scattered laterally and arrives as laterally scattered radiation 36' at the radiation receiver 35', or is reflected and arrives as backscattered radiation 38' at the radiation receiver 37'. As described in respect of the exemplary embodiment according to FIG. 4, according to the spatial arrangement of the individual elements of the sensor unit 10, in accordance with this exemplary embodiment, as seen from the radiation 32' emitted by the radiation source 31', the angle between the radiation source 31' and the radiation receiver 33' for determining the transmitted radiation quantity 34' is essentially 180°, the angle between the radiation source 31' and the radiation receiver 35' for determining the laterally scattered radiation quantity 36' is essentially 90°, and the angle between the radiation source 31' and the radiation receiver 37' for determining the backscattered radiation quantity 38' is essentially 0°. Also according to the exemplary embodiment described in FIG. 4, in order to avoid direct irradiation by the radiation source 31' of the radiation receiver 37' for determining the backscattered radiation quantity 38', which radiation receiver should be arranged as close as possible to the radiation source 31', a shield 41 is provided between the radiation source 31' and the radiation receiver 37'. In contrast to the exemplary embodiment described in FIG. 4, in this exemplary embodiment the three radiation receivers 33', 35' and 37' have in each case three radiation receivers 33'a, 33'b, 33'c, 35'a, 35'b, 35'c, 37'a, 37'b, 37'c which are assigned to the different wavelength ranges and which are activated in succession, according to the associated wavelength ranges, by the control and evaluation unit 39, so that the radiation 34', 36', 38' is detected and determined, in each case in succession, by the in each case three radiation receivers 33'a, 33'b, 33'c, 35'a, 35'b, 35'c, 37'a, 37'b, 37'c. As a result, the radiation quantities measured in each case by means of the radiation receivers 33', 35' and 37' can be assigned unequivocally to a wavelength to be measured. As in the exemplary embodiment according to FIG. 4, the evaluation of the current values generated by the measured values takes place in such a way that, in this exemplary embodiment too, the washing program is optimized with respect to the determined characteristics of the dirt components and/or cleaning agent components, for example by controlling the addition of cleaning agents, the washing liquid quantity, the change of washing liquid and the temperature and duration of the washing program or of a corresponding sub-program step of the washing program of the dishwasher.

In the two exemplary embodiments shown, radiation 32, 32' is emitted in the wavelength ranges, in which the dirt component and/or cleaning agent component of the washing liquid 40, the type and concentration of which component are to be determined, leads to a pronounced attenuation and/or scattering of the irradiated radiation 32, 32', the radiation 32, 32' being emitted in each wavelength range essentially in the range of one wavelength and being delimited as accurately as possible.

In the two exemplary embodiments shown, the radiation-source 31, 31' is operated in the pulsed mode in order to increase the signal levels of the control and evaluation unit 39. The radiation quantity received by the radiation receivers 33, 33', 35, 35', 37, 37' is then measured synchronously with the emitted pulses. Furthermore, in the two exemplary embodiments shown, both the radiation source 31, 31' and the radiation receivers 33, 33', 35, 35', 37, 37' are connected to the control and evaluation unit 39 via connecting lines.

By means of the method according to the invention, described above in two exemplary embodiments, optimization of the washing program in dishwashers is achieved by obtaining more accurate data relating to the dirt components and/or cleaning agent components of the washing liquid 40. These data allow the washing program to be controlled more effectively, thereby saving energy and water used by the dishwasher.

We claim:

1. A method for treating dishes in a dishwasher, which comprises:

radiating a radiation into a washing liquid in a given direction;

detecting a radiation quantity of a radiation emerging from the washing liquid substantially in the given direction, of a radiation emerging as a scattered radiation from the washing liquid substantially perpendicular to the given direction, and of a radiation emerging as a backscattered radiation from the washing liquid substantially opposite to the given direction for at least a given wavelength range;

processing signals representing the detected radiation quantity;

based upon the signals, determining data selected from the group consisting of a type, a concentration, and a prevailing size of the group consisting of a dirt component in the washing liquid, a cleaning agent component in the washing liquid, and suspended particles in the washing liquid based upon the detected radiation quantity of the emerging radiation; and optimizing a washing program with the determined data.

2. The method according to claim 1, wherein the given wavelength range is substantially a wavelength range of a single wavelength.

3. The method according to claim 1, wherein the step of determining data is further based on a radiation quantity of the radiation radiated into the washing liquid.

4. The method according to claim 1, wherein the radiation radiated into the washing liquid includes at least the given wavelength range, and wherein the radiation quantity of the radiation emerging from the washing liquid is determined by at least one broadband radiation receiver sensitive to a wide wavelength range including the given wavelength range.

5. The method according to claim 1, wherein the radiation radiated into the washing liquid is generated by a plurality of radiation sources, the given wavelength range including a plurality of partial wavelength ranges, and the given partial wavelength ranges being generated by a respective one radiation source of the plurality of radiation sources.

6. The method according to claim 1, wherein the radiation radiated into the washing liquid includes at least the given wavelength range, and wherein the radiation quantity of the radiation emerging from the washing liquid is determined by at least one radiation receiver sensitive to the given wavelength range.

7. The method according to claim 1, wherein the radiation radiated into the washing liquid is generated by a broadband radiation source generating all wavelength ranges to be emitted.

8. The method according to claim 1, wherein the radiation radiated into the washing liquid is emitted in at least one wavelength range, in which the at least one of a dirt component, a cleaning agent component, and suspended particles in the washing liquid causes at least one of a pronounced attenuation and scattering of the radiation radiated into the washing liquid.

9. The method according to claim 1, wherein the step of radiating the radiation into the washing liquid includes sequentially emitting a first wavelength range and a second wavelength range.

10. The method according to claim 1, wherein the step of detecting includes sequentially detecting the radiation quantity of a radiation having a first wavelength range and detecting the radiation quantity of a radiation having a second wavelength range.

11. The method according to claim 1, wherein the radiation radiated into the washing liquid is emitted in a pulsed manner.

12. The method according to claim 1, wherein the radiation radiated into the washing liquid is emitted with a wavelength range of substantially a single wavelength.

13. The method according to claim 1, wherein the radiation radiated into the washing liquid is guided to the washing liquid by a radiation guide.

14. The method according to claim 1, wherein the radiation emerging from the washing liquid is guided to at least one radiation receiver via a radiation guide.

15. A device for determining at least one of a type, a concentration, and a prevailing size of at least one of a dirt component, a cleaning agent component, and suspended particles in a washing liquid of a dishwasher, comprising:

a radiation source for emitting radiation in a given direction within a given wavelength range into a washing liquid;

a radiation receiver for determining a radiation quantity of a radiation backscattered in the washing liquid substantially opposite said given direction and at least one of a radiation transmitted through the washing liquid and a radiation laterally scattered in the washing liquid, and generating a signal corresponding to said radiation quantity; and a control and evaluation unit for evaluating the signal from said radiation receiver, said control and evaluation unit connected to said radiation receiver.

16. The device according to claim 15, wherein said given wavelength range is a wavelength range of a single wavelength.

17. The device according to claim 17, wherein said radiation source emits said radiation in a given direction, said radiation receiver including a first radiation receiver for determining said radiation quantity of said transmitted radiation at an angle of substantially 180° with respect to said given direction, a second radiation receiver determining said radiation quantity of said laterally scattered radiation at an angle of substantially 90° with respect to said given direction, and a third radiation receiver determining said radiation quantity of said backscattered radiation at an angle of substantially 0° with respect to said given direction.

18. The device according to claim 15, further comprising a flow heater, said radiation source and said radiation receiver forming a sensor unit, said sensor unit disposed in said flow heater.

19. The device according to claim 18, further comprising a receptacle, said sensor Unit placed in said receptacle.

20. The device according to claim 19, wherein said flow heater has a separate receiving connection piece for receiving said sensor unit placed in said receptacle, said receptacle being formed from at least a milky-transparent material, being completely closed at an end thereof projecting into said flow heater, and having a substantially round cross section.

21. The device according to claim 18, further comprising a printed circuit board having two side legs and one connecting leg and having a U-shaped recess formed therein, said sensor unit being fastened on said printed circuit board, wherein said radiation receiver includes a plurality of radiation receivers, each respective one of said radiation receivers disposed on a respective one of said side legs and said connecting leg and directed toward said U-shaped recess, said radiation source disposed on one of said side legs.

22. The device according to claim 21, wherein said receptacle has two legs disposed at a given distance from one another, said side legs of said printed circuit board disposed in said legs of said receptacle, said legs of said receptacle having a cross-sectional shape of two circle segments resting with chords thereof against one another, said receptacle having wall portions, behind which said radiation receivers and said radiation source are disposed, said wall portions having a wall thickness less than a wall thickness of a remaining part of said receptacle.

23. The device according to claim 21, wherein said receptacle has at least one guide, into which said printed circuit board can be inserted, said guide including holding ribs disposed in pairs at a distance from one another corresponding to a thickness of said printed circuit board.

24. The device according to claim 19, further comprising a radiation guide for guiding said radiation radiated into the washing liquid from said radiation source to said receptacle.

25. The device according to claim 19, further comprising a radiation guide for guiding said radiation emerging from the washing liquid from said receptacle to said radiation receiver.

* * * * *